US007245438B2

(12) United States Patent
Chuang et al.

(10) Patent No.: US 7,245,438 B2
(45) Date of Patent: Jul. 17, 2007

(54) BROAD BAND OBJECTIVE HAVING IMPROVED LATERAL COLOR PERFORMANCE

(75) Inventors: Yung-Ho Chuang, Cupertino, CA (US); David R. Shafer, Connecticut, CA (US); J. Joseph Armstrong, Milpitas, CA (US)

(73) Assignee: KLA-Tencor Technologies Corporation, Mipitas, CA (US)

( * ) Notice: Subject to any disclaimer, the term of this patent is extended or adjusted under 35 U.S.C. 154(b) by 0 days.

(21) Appl. No.: 11/245,591

(22) Filed: Oct. 5, 2005

(65) Prior Publication Data

US 2006/0262418 A1 Nov. 23, 2006

Related U.S. Application Data

(60) Provisional application No. 60/683,886, filed on May 23, 2005.

(51) Int. Cl.
  *G02B 3/00* (2006.01)
(52) U.S. Cl. .................... 359/642; 359/362; 359/896

(58) Field of Classification Search ................ 359/435, 359/362, 642, 896
See application file for complete search history.

(56) References Cited

U.S. PATENT DOCUMENTS

| 5,888,193 | A  | * | 3/1999 | Breidenthal et al. ........ 600/160 |
| 5,933,275 | A  | * | 8/1999 | Igarashi .................... 359/435 |
| 6,545,802 | B2 | * | 4/2003 | Hoogland .................. 359/435 |
| 2004/0125446 | A1 | * | 7/2004 | Lei ........................... 359/435 |

* cited by examiner

*Primary Examiner*—Scott J. Sugarman
*Assistant Examiner*—Darryl J. Collins
(74) *Attorney, Agent, or Firm*—Smyrski Law Group, A P.C.

(57) ABSTRACT

A system and method for inspection is disclosed. The design generally employs as many as four design principles, including employing at least one lens from a relatively low dispersion glass, at least one additional lens from an additional material different from the relatively low dispersion glass, generally matching the relatively low dispersion properties of the relatively low dispersion glass. The design also may include at least one further lens from a further material different from and exhibiting a significantly different dispersion power from the relatively low dispersion glass and the additional material. Finally, the design may include lenses positioned to insert a significant amount of color within the objective, a gap, and additional lenses, the gap and additional lenses serving to cancel the color inserted.

21 Claims, 5 Drawing Sheets

BROAD BAND OBJECTIVE HAVING IMPROVED LATERAL COLOR PERFORMANCE

This application claims the benefit of U.S. Provisional Patent Application 60/683,886, "Broad band Objective Having Improved Lateral Color Performance," inventors Yung-Ho Chuang et al., filed May 23, 2005.

BACKGROUND OF THE INVENTION

1. Field of the Invention

The present invention relates generally to the field of optical imaging, and more specifically to optical systems used for microscopic imaging, inspection, metrology and lithography applications.

2. Description of the Related Art

Many optical systems have the ability to inspect or image features on the surface of a specimen, such as inspecting defects on a semiconductor wafer or photomask, or alternately examining a biological specimen on a slide. Microscopes have been used in various imaging situations, including biology, metrology, semiconductor inspection, and other complex inspection applications where high resolution images of small areas and/or features are desired.

When inspecting features on a specimen surface, a broadband objective exhibiting highly accurate and near perfect optical performance is particularly desirable. This is particularly true for alignment systems such as those used for photomask alignment. However, all standard objectives are typically limited at the edge of the field by lateral color.

In general, lateral color represents a difference between different wavelengths of light, such as blue light and red light. FIG. 1 shows the principal ray of an optical system formed from a positive lens 101. Blue light ray 102 in this simple arrangement tends to be more strongly refracted than red light ray 103 due to the refractive index changing with wavelength. The difference in position of the rays is the lateral color 104, a standard definition based on the principal ray position. Note that the standard definition for lateral color does not include the effects of monochromatic aberrations such as coma and chromatic variation of coma. These aberrations can move the image centroid away from the principal ray location. Monochromatic aberrations and the chromatic variation of the monochromatic aberrations produce an additional contribution to lateral color when based on such an image centroid definition.

Lateral color according to this centroid definition can yield problems when inspecting under precise conditions. In other words, lateral color causes a shift in the image centroid for different colors. The centroid shift can adversely impact the image, particularly at the edge of the field. Lateral color can also limit the accuracy obtained when using optics in metrology applications.

Some new methods for high order color correction can reduce the effects of lateral color and the aforementioned chromatic centroid shift to less than 1 nanometer (nm) over a very broad wavelength range, generally improving the image at the edge of the field. As centroid shift can vary for different colors, a design where the centroid shift for all colors is reasonably uniform can be highly desirable, particularly when changing the focus position for the image.

It would therefore be beneficial to provide a system for use in microscopy that overcomes the foregoing lateral color drawbacks present in previously known systems and provide an optical inspection or metrology system design having improved functionality over devices exhibiting those negative aspects described herein.

SUMMARY OF THE INVENTION

According to a first aspect of the present design, there is provided a high order color correction specimen inspection or metrology apparatus. The apparatus comprises at least one lens constructed from a relatively low dispersion glass, at least one additional lens constructed from an additional material different from the relatively low dispersion glass of the at least one lens. The apparatus further comprises at least one further lens constructed from a further material different from the relatively low dispersion glass and the additional material. A first plurality of lenses is positioned on one side of a gap and a second plurality of lenses is positioned on another side of the gap. The first plurality of lenses causes an introduction of a significant amount of color, and the gap and second plurality of lenses substantially cancel the significant amount of color.

These and other aspects of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

Figure 1:
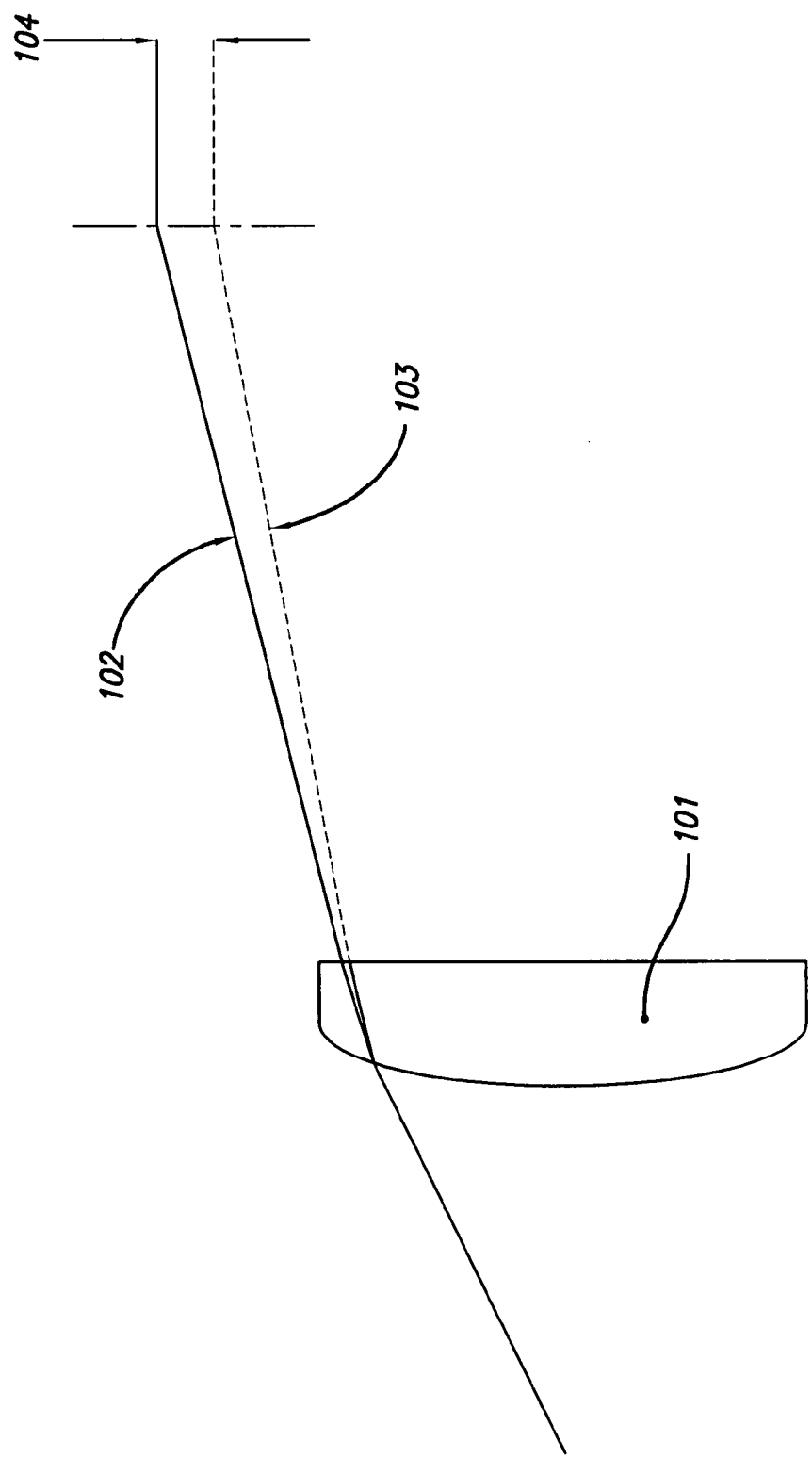
FIG. 1 represents the problem of lateral color addressed by the present design.

The present design employs a new method to reduce the amount of lateral color in an optical system. Lateral color is created within an optical system because of the natural dispersion properties of glass materials used to make lenses. This dispersion causes different wavelengths to form images at different locations and having different amounts of monochromatic aberrations. This dispersion creates a shift in the image centroid position for each wavelength. Using this new method, a lens may be provided within the design to produce a significant amount of color, and subsequently canceling the color using a relatively large airspace between the first lens and another lens with a controlled amount of color. In this manner, lateral color effects can be reduced and, in particular, centroid shifting due to different colors can be minimized.

Many refractive optical designs have been developed having a broad spectral range or band for the illumination employed. Typical inspection systems employ an illuminator transmitting illumination energy at one or more wavelengths, and optics generally designed to particularly focus and efficiently utilize the transmitted illumination energy. Many different illumination sources, including but not limited to broadband light sources and lasers have been employed. When the illuminators and other inspection components exhibit shorter focal lengths, such as in the case of microscope objectives, color aberrations can become very limiting to the lens resolution when covering a broad spectral band.

If the highest possible color and aberration correction is required, over a broad band, four general design principles may be employed.

The first design principle minimizes the color present inside the system, where inside the system represents within the optical components used to inspect the specimen. Color minimization entails providing the smallest possible amount of color, thereby minimizing the lateral color correction required. Color minimization occurs when most of the positive power in the design, especially near the aperture stop, is constructed from a very low dispersion glass—ideally calcium fluorite, FPL51, FPL53 or a close approximation to such a low dispersion glass type. Such glasses are generally available from high precision lens manufacturers and are known by these designations to those skilled in the art. Use of glasses, lenses, and/or optical components of this type provides a relatively small amount of color that may then be corrected by other components within the design.

The second design principle is to correct the minimized color present using a different glass that matches very well with respect to the higher-order dispersion properties of the first glass type. If this design principle is followed, the secondary and higher order color residuals will generally be relatively small. For example, for FPL51 glass, a very good match exists with respect to higher-order dispersion properties in silica. Thus using negative lenses fabricated from silica may beneficially correct the color of the positive lenses, such as those of Ohara FPL51 glass, and may provide very little residual higher-order color.

Use of different matched glasses in this manner can sufficiently correct color for positive lenses. However, in high NA designs, a minimal dispersion difference exists between FPL51 glass and silica, thus requiring certain relatively strong power lenses with steep radii in order to obtain adequate color correction. In a high NA design, total internal reflection and adverse monochromatic aberrations tend to be prevalent. Both of these problems may be diminished if the negative silica lenses are attached to the positive FPL51 lenses, such as by using cement or other adhesive. The result of cementing lenses, for example, may be that the cemented interface between these two low index glasses does not provide a significant amount of monochromatic aberration correction as the two glass index values are too similar. The present design addresses monochromatic aberration issues by using other non-joined lenses perform monochromatic aberration correction. Using other non-joined lenses can increase the complexity of the design.

An alternative method calls for the negative lenses in the design to exhibit a slightly higher index than the FPL51 positive lenses. This allows the design to achieve some monochromatic aberration correction at the cemented interface. Monochromatic aberration correction at the cemented interface results in the FPL51 positive lenses not having color corrected by the silica glass. Negative lenses used in the present design, typically constructed of Ohara BSL7, tend to be a good match in higher-order dispersion properties to FPL51, but not a perfect match. The result is that over a very broad spectral range, the design may exhibit large residual color aspects that may be unacceptable in many applications.

The third design principle employs the "dense-flint" principle to correct higher-order color aberrations. The dense-flint principle involves the use of a relatively small amount of lens power with a glass that has a very different higher-order dispersion property from the previous two glasses, where the previous two glasses are well matched in higher order dispersion characteristics. Usually the glass having the different higher-order dispersion property is a very high index flint glass that is highly dispersive. In the present design, one embodiment may include the glass Ohara TIH 11. The use of a small amount of power of this very different higher-order dispersion properties glass in the design allows for a very beneficial enhancement of residual color aberrations and can give correction for secondary and even tertiary color effects. Use of a glass such as a very high index flint glass can correct higher-order lateral color effects if the glass is positioned in the design at a relatively remote distance from the aperture stop. Positioning the glass at a relatively remote distance from the aperture stop can control higher-order paraxial lateral color to compensate for chromatic variation of coma. Coma is a type of lateral color that depends on the aperture and is not paraxial.

The new design principle used in these embodiments to correct the majority of the residual centroid based lateral color is to introduce a relatively large amount of color in the middle section of the design using either a positive or negative lens or lens group and then cancel the large amount of color using a relatively large airspace between the components that put in the color and those that subsequently cancel the color out. These subsequent components have a total power that is of the opposite sign to the group producing the color. Inserting an abundance of color between separated components makes for different ray heights and angles for each color. By the time these rays reach the second optical or downstream component group, the result is a chromatic variation in spherical aberration and coma. Chromatic variations represent an induced effect due to aberrations between design components. These chromatic variations are not an effect substantially intrinsic to the surfaces. In very highly corrected designs, these induced effects can be as important as aberrations intrinsic to the surfaces and can thus materially affect the resultant image or images. In the present design, the introduction of significant color in the large middle airspace of the design allows the resulting induced chromatic variation of spherical aberration and coma to correct for the intrinsic aberrations of that type using the rest of the components in the design. The result is a very highly corrected high NA design, with extremely good performance.

If system length is not of significant concern, then the relatively long airspace in the middle of the design could be nearly collimated and a stretched-out design could be very well corrected using the foregoing design principles. But if a short design is required, the airspace in the middle of the design must be in fairly strongly converging light.

Other designs exhibiting similar correction tendencies may be achievable according to the foregoing principles, but the results are generally sensitive to the glass choices.

Figure 2:
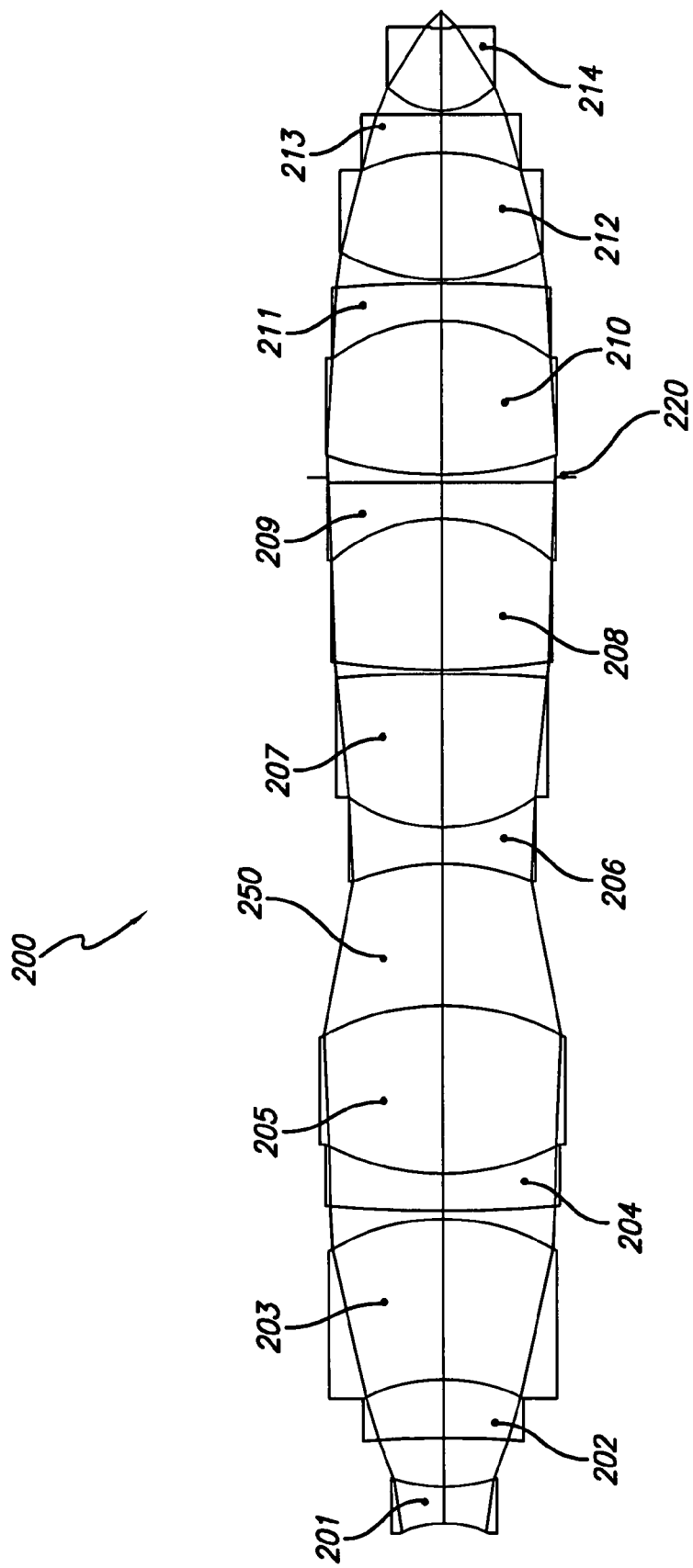
FIG. 2 is a 0.7 NA design using FPL51 for the positive elements, where lateral color from 488 to 720 nm is less than 1 nm at the edge of a 50 micron diameter field.
Figure 3:
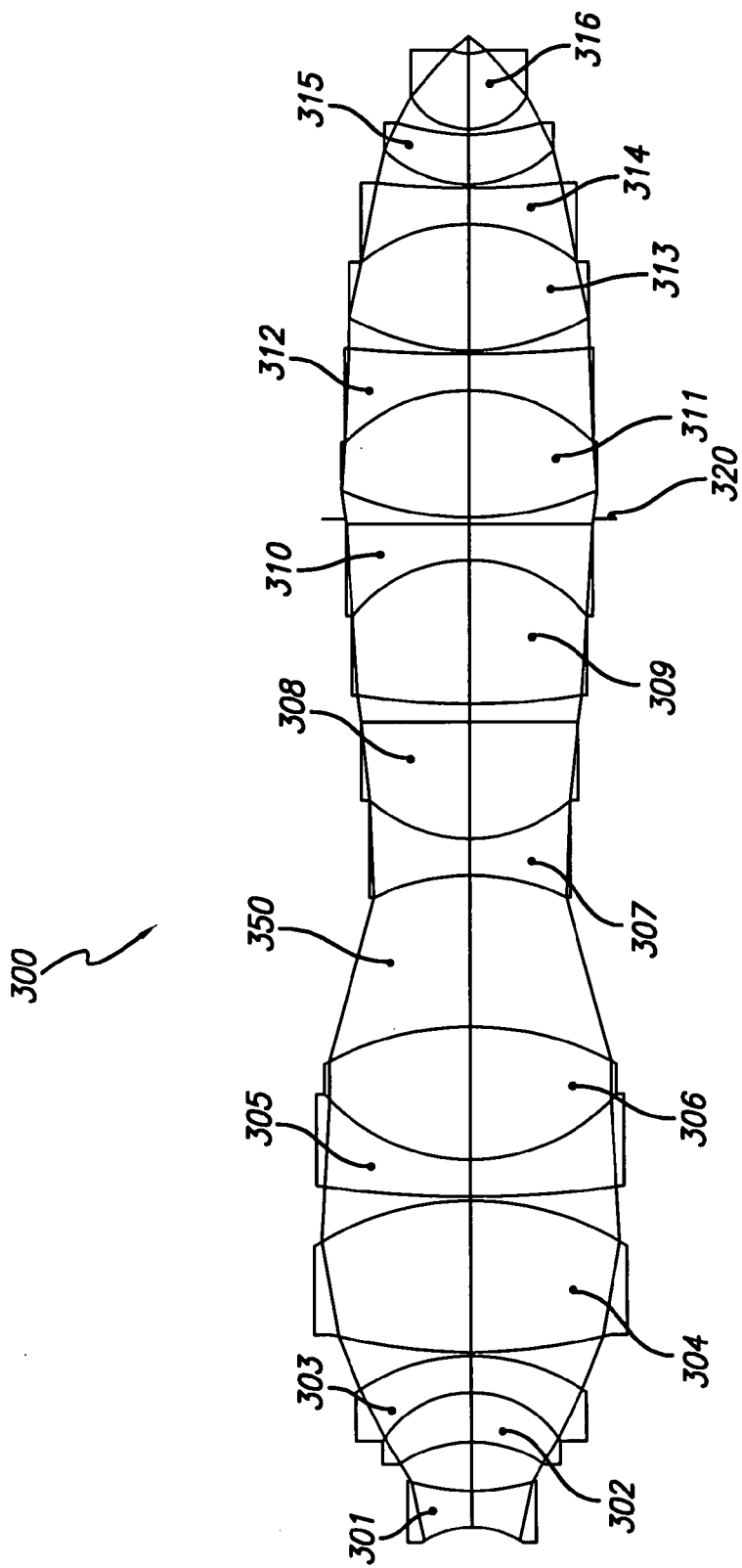
FIG. 3 shows a 0.8 NA design using FPL51 glass for the positive elements, where lateral color from 488 to 720 nm is less than 1 nm at the edge of a 50 micron diameter field.
Figure 4:
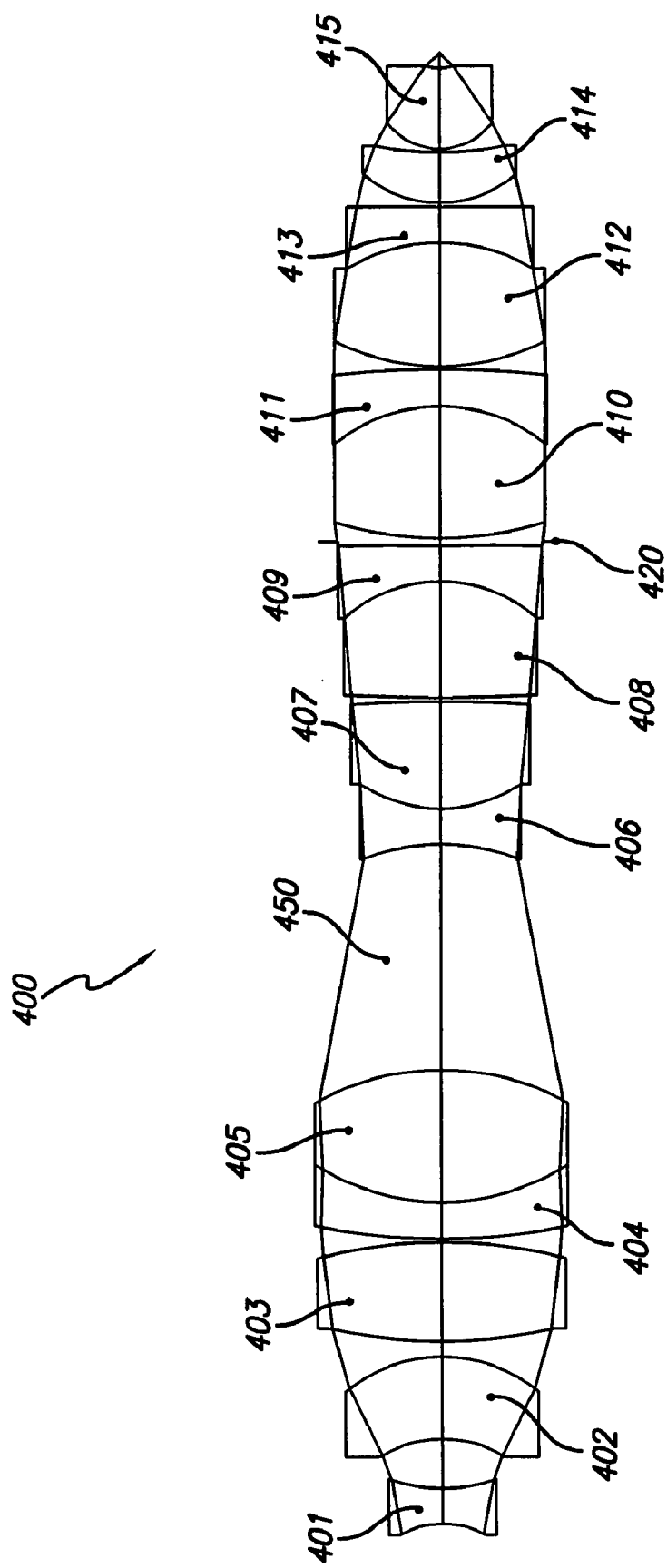
FIG. 4 illustrates a 0.8 NA design using FPL53 for the positive elements, where the FPL53 glass has a lower dispersion than the FPL51 glass, and lateral color from 488 to 720 nm is less than 1 nm at the edge of a 50 micron diameter field.

Various examples of designs adhering to the foregoing principles are illustrated in FIGS. 2–4. FIG. 2 is a 0.7 NA design using FPL51 for the positive elements. The lateral color from 488 to 720 nm is less than 1 nm at the edge of a 50 micron diameter field.

TABLE 1

Prescription for the design of FIG. 2.

| | Radius | Thickness | Glass |
|---|---|---|---|
| OBJ | Infinity | Infinity | |
| 1 | −3.45081 | 1.1 | S-FPL51 |
| 2 | 4.83798 | 1.5 | |
| 3 | −15.9467 | 1.74991 | S-TIH11 |
| 4 | −4.88786 | 4.729387 | S-FPL51 |
| 5 | −6.4339 | 0.25 | |
| 6 | 51.1452 | 1.1 | BAM21 |
| 7 | 7.238453 | 4.999964 | S-FPL51 |
| 8 | −7.45296 | 4.181398 | |
| 9 | −6.9446 | 1.1 | BAM21 |
| 10 | 4.811282 | 4.5 | S-FPL51 |
| 11 | −37.7316 | 0.109924 | |
| 12 | 20.77116 | 4.5 | S-FPL51 |
| 13 | −4.82976 | 1.1 | S-BSL7 |
| 14 | 3905.813 | 0.101135 | |
| STO | Infinity | 0.11 | |
| 16 | 10.95898 | 4.5 | S-FPL51 |
| 17 | −5.27083 | 1.1 | S-BSL7 |
| 18 | −40.9304 | 0.11 | |
| 19 | 5.928153 | 3.75 | S-FPL51 |
| 20 | −5.27979 | 1.1 | S-BSL7 |
| 21 | 1338.503 | 0.11 | |
| 22 | 2 | 2.459581 | S-FPL51 |
| 23 | 2.704 | 0.500003 | |
| IMA | Infinity | | |

The foregoing table reads the various components in FIG. 2 from left to right. As may be appreciated by one skilled in the art, the numbers in the leftmost column of Table 1 represent the surface number counting surfaces from the left of FIG. 2. For example, the left surface of lens 201 in the orientation presented in FIG. 2 (surface 1 in Table 1) has a radius of curvature of −3.45081 mm, a thickness of 1.1 mm, and the rightmost surface (surface 2) has a radius of curvature of 4.83798 mm, and is 1.5 mm from the nest surface. The material used is S—FPL51, or FPL51. The designation STO represents the aperture stop, IMA the image, and OBJ the objective.

Stepping through the lenses of the objective design 200 of FIG. 2, from left to right, first lens 201 is constructed of FPL51, while second lens 202 is formed from flint glass TIH 11. Third lens 203 is formed of FPL51. Fourth lens 204 is formed of BAM21, while fifth lens 205 is constructed of FPL51. Gap 250 is formed between fifth lens 205 and sixth lens 206, where sixth lens 206 is formed from BAM21. Seventh lens 207 is constructed of FPL51, as is eighth lens 208. Ninth lens 209 is formed from BSL7, while tenth lens 210 uses FPL51, eleventh lens 211 BSL7, twelfth lens 212 FPL51, thirteenth lens 213 BSL7, and fourteenth lens 214 FPL51. Aperture stop 220 is shown between ninth lens 209 and tenth lens 210. Note that the net power in the first plurality of lenses, namely first lens 201 through fifth lens 205, is opposite in sign from the second plurality of lenses, namely sixth lens 206 through fourteenth lens 214. For example, the first plurality may be positive while the second is negative, or vice versa.

The present design employs optical cement where two elements are in contact with one another. In the embodiment of FIG. 2, cement is provided between lens elements 202 and 203, lens elements 204 and 205, lens elements 206 and 207, lens elements 208 and 209, lens elements 210 and 211, and lens elements 212 and 213. UV cure epoxies specially developed for this application are typically used, but other types of cement are possible.

In this construction, the four principles noted earlier apply as follows. The first principle, color minimization, occurs when most of the positive power in the design, especially near the aperture stop, is constructed from a very low dispersion glass. As shown in FIG. 2, seventh, eighth, tenth, and twelfth lenses 207, 208, 210, and 212 are positioned near the aperture stop, and seventh lens 207, eighth lens 208, tenth lens 210, and twelfth lens 212 are constructed from low dispersion FPL51. The design of FIG. 2 also corrects the color present using a different glass that matches very well with respect to the higher-order dispersion properties of the first glass type. Here the first glass type is FPL51, and the matching glass is BSL7, again a material known to those skilled in the precision glassmaking art and familiar with Ohara types and Ohara codes. The design of FIG. 2 further employs dense flint principle, the third principle noted above, where the dense flint glass TIH11 is used in lens 202. Finally, the design of FIG. 2 introduces a relatively large amount of color in the middle section of the design, and then cancels the large amount of color using a relatively large airspace between the components that insert the color and those that subsequently cancel the color out. Gap 250 separates lenses that introduce color, namely lenses 201–205, from those that remove the color, generally lenses 206–214. In this manner, a design that minimizes lateral color issues may be FIG. 3 is a 0.8 NA design using FPL51 glass for the positive elements, again reflecting the four foregoing principles. The lateral color in the wavelength range from 488 to 720 nm is less than 1 nm at the edge of a 50 micron diameter field.

TABLE 2

Prescription for the design of FIG. 3.

| Surf | Radius | Thickness | Glass |
|---|---|---|---|
| OBJ | Infinity | Infinity | |
| 1 | −2.640033 | 1.1 | S-FPL51 |
| 2 | 6.225586 | 1.5 | |
| 3 | −3.883463 | 1.499939 | S-TIH11 |
| 4 | −3.196875 | 1.1 | S-FPL51 |
| 5 | −6.06235 | 0.11 | |
| 6 | 17.79942 | 4.55255 | S-FPL51 |
| 7 | −8.693053 | 0.11 | |
| 8 | 34.32157 | 1.1 | BAM21 |
| 9 | 5.894936 | 3.999935 | S-FPL51 |
| 10 | −9.132433 | 4.52315 | |
| 11 | −6.94491 | 1.1 | BAM21 |
| 12 | 4.646253 | 3.500181 | S-FPL51 |
| 13 | 578.2921 | 0.561037 | |
| 14 | 23.67839 | 4.27221 | S-FPL51 |
| 15 | −4.621956 | 1.1 | S-BSL7 |
| 16 | 1993.301 | 0.102457 | |
| STO | Infinity | 0.11 | |
| 18 | 10.09419 | 3.749717 | S-FPL51 |
| 19 | −5.356311 | 1.1 | S-BSL7 |
| 20 | 47.25849 | 0.1099999 | |
| 21 | 7.107647 | 3.75 | S-FPL51 |
| 22 | −5.312922 | 1.1 | S-BSL7 |
| 23 | 33.19032 | 0.11 | |
| 24 | 3.66806 | 1.5 | S-FPL51 |
| 25 | 8.445074 | 0.11 | |
| 26 | 2 | 2.297492 | S-FPL51 |
| 27 | 2.040446 | 0.5000674 | |
| IMA | Infinity | | |

From FIG. 3, objective 300 includes first lens 301 which is formed of FPL51, second lens 302 is formed from flint glass TIH11, third lens 303 from FPL51, and fourth lens 304 from FPL51. Fifth lens 305 is constructed from BAM21, sixth lens 306 from FPL51, seventh lens 307 from BAM21, eighth lens 308 from FPL51, and ninth lens 309 from FPL51, and the tenth lens 310 from BSL7. Aperture stop 320 is provided, and gap 350 is provided between sixth lens 306 and seventh lens 307. Eleventh lens 311 is constructed from FPL51, Twelfth lens 312 from BSL7, thirteenth lens 313 from FPL51, and Fourteenth lens 314 from BSL7. Fifteenth lens 315 is formed from FPL51, and sixteenth lens 316 is formed from FPL51 Again the lenses that are in contact, namely lens 302 and 303, lenses 305 and 306, lenses 307 and 308, lenses 309 and 310, lenses 311 and 312, and lenses 313 and 314 are cemented together.

FIG. 4 is a 0.8 NA design using FPL53 for the positive elements. This glass has a lower dispersion than the FPL51 glass. The lateral color in the wavelength range from 488 to 720 nm is less than 1 nm at the edge of a 50 micron diameter field.

TABLE 3

Prescription for the design of FIG. 4.

| Surf | Radius | Thickness | Glass |
|---|---|---|---|
| OBJ | Infinity | Infinity | |
| 1 | −2.70283 | 1.1 | S-FPL53 |
| 2 | 5.399748 | 1.5 | |
| 3 | −3.44088 | 2.509086 | S-TIH11 |
| 4 | −4.46521 | 0.495999 | |
| 5 | 17.47191 | 2.974508 | S-FPL53 |
| 6 | −15.0158 | 0.11 | |
| 7 | 19.85473 | 1.1 | BAM4 |
| 8 | 6.98409 | 4.00001 | S-FPL53 |
| 9 | −7.98404 | 6.914389 | |
| 10 | −6.78548 | 1.1 | BAM4 |
| 11 | 4.448233 | 3.25 | S-FPL53 |
| 12 | −31.1679 | 0.110758 | |
| 13 | 93.80093 | 3.5 | S-FPL53 |
| 14 | −4.38537 | 1.1 | FSL3 |
| 15 | −153.15 | 0.099999 | |
| STO | Infinity | 0.11 | |
| 17 | 11.09318 | 4 | S-FPL53 |
| 18 | −5.03763 | 1.1 | FSL3 |
| 19 | −38.0933 | 0.11 | |
| 20 | 7.069142 | 3.75 | S-FPL53 |
| 21 | −5.55846 | 1.1 | FSL3 |
| 22 | −177.003 | 0.11 | |
| 23 | 3.597066 | 1.5 | S-FPL53 |
| 24 | 9.624745 | 0.11 | |
| 25 | 2 | 2.432919 | S-FPL53 |
| 26 | 1.719818 | 0.49998 | |
| IMA | Infinity | | |

From FIG. 4, objective 400 comprises first lens 401 formed of FPL53. Second lens 402 is formed from flint glass TIH11, third lens 403 from FPL53, and fourth lens 404 from BAM4. Fifth lens 405 is constructed from FPL53, sixth lens 406 from BAM4, seventh lens 407 from FPL53, eighth lens 408 from FPL53, and ninth lens 409 from FSL3. Aperture stop 420 is provided, and gap 450 is provided between fifth lens 405 and sixth lens 406. Tenth lens 410 is constructed from FPL53, eleventh lens 411 from FSL3, twelfth lens 412 from FPL53, and thirteenth lens 413 from FSL3. Fourteenth lens 414 and fifteenth lens 415 are both formed from FPL53. Again, this design follows the four foregoing principles, using low dispersion glass FPL53, matching glass FSL3, flint glass TIH11, and providing gap 450, such that lenses 401–405 introduce significant color while lenses 406–415 remove the color.

Figure 5:
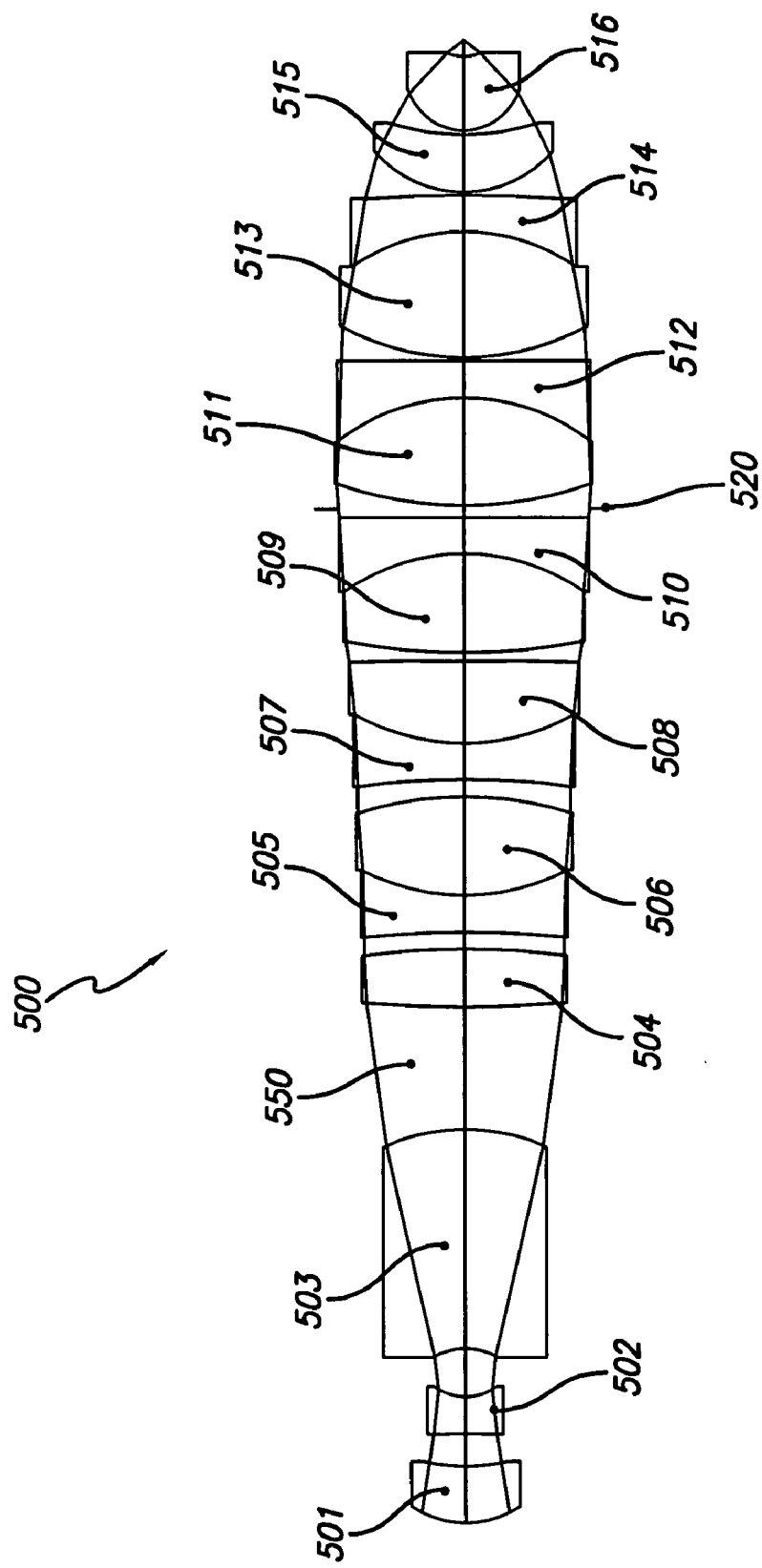
FIG. 5 is a further 0.8 NA design using FPL53 for the positive elements, where lateral color in the wavelength range from 488 to 720 nm is less than 1 nm at the edge of a 50 micron diameter field.

FIG. 5 is a further 0.8 NA design using FPL53 for the positive elements. This glass has a lower dispersion than the FPL51 glass. The lateral color in the wavelength range from 488 to 720 nm is less than 1 nm at the edge of a 50 micron diameter field.

TABLE 4

Prescription for the design of FIG. 5.

| Surf | Radius | Thickness | Glass |
|---|---|---|---|
| OBJ | Infinity | Infinity | |
| 1 | 3.295736 | 1.749972 | S-BSL7 |
| 2 | 7.600172 | 1 | |
| 3 | −26.95779 | 1.1 | S-FPL53 |
| 4 | 1.84435 | 1.5 | |
| 5 | −2.251053 | 6.687232 | S-FPL53 |
| 6 | −6.093807 | 3.723266 | |
| 7 | 47.76675 | 1.75 | S-TIH11 |
| 8 | −23.67633 | 0.5 | |
| 9 | −31.96948 | 1.1 | S-BAM4 |
| 10 | 7.165765 | 3 | S-FPL53 |
| 11 | −10.76491 | 0.5 | |
| 12 | −23.64424 | 1.1 | S-BAM4 |
| 13 | 7.45945 | 2.5 | S-FPL53 |
| 14 | −108.5253 | 0.25 | |
| 15 | 20.66576 | 3 | S-FPL53 |
| 16 | −6.61093 | 1.1 | FSL3 |
| 17 | Infinity | 0.25 | |
| STO | Infinity | 0.11 | |
| 19 | 12.09707 | 3.25 | S-FPL53 |
| 20 | −6.469096 | 1.1 | FSL3 |
| 21 | −2134.371 | 0.1099999 | |
| 22 | 8.354132 | 3.75 | S-FPL53 |
| 23 | −6.302046 | 1.1 | FSL3 |
| 24 | −42.86506 | 0.11 | |
| 25 | 3.734808 | 1.75 | S-FPL53 |
| 26 | 8.546036 | 0.11 | |
| 27 | 1.8 | 2.249545 | S-FPL53 |
| 28 | 1.492067 | 0.5 | |
| IMA | Infinity | | |

From FIG. 5, objective 500 comprises first lens 501 formed of BSL7. Second lens 502 is formed from flint FPL53, third lens 503 from FPL53, and fourth lens 504 from flint glass TIH11. Fifth lens 505 is constructed from BAM4, sixth lens 506 from FPL53, seventh lens 507 from BAM4, eighth lens 508 from FPL53, and ninth lens 509 from FPL53. Aperture stop 520 is provided, and gap 550 is provided between third lens 503 and fourth lens 504. Tenth lens 510 is constructed from FSL3, eleventh lens 511 from FPL53, twelfth lens 512 from FSL3, and thirteenth lens 513 from FPL53 and the fourteenth lens from FSL3. Fifteenth lens 515 and sixteenth lens 516 are both formed from FPL53. Again, this design follows the four foregoing principles, using low dispersion glass FPL53, matching glass FSL3, flint glass TIH11, and providing gap 550, such that lenses 501–503 introduce significant color while lenses 504–515 remove the color. This design demonstrates using a negative lens group consisting of elements 501 through elements 503 introducing color that is compensated by positive lens group 504–515.

The present design may be employed in various environments, including but not limited to semiconductor wafer inspection/lithography, biological inspection, medical research, and the like.

While the invention has been described above by reference to certain embodiments, it will be understood that changes and modifications may be made without departing from the scope of the invention, which is to be defined only by the appended claims and their equivalents. For example, while the embodiments are illustrated with respect to specific lensing arrangements conforming to certain principles, the invention may be constructed in other ways and used in inspecting various types of specimens, including but not limited to semiconductor masks, wafers and other lithography applications, biological specimens, and so forth. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for providing high order color correction inspection of a specimen, comprising:
    constructing at least one lens from a relatively low dispersion glass;
    further constructing at least one additional lens from an additional material different from the relatively low dispersion glass of the at least one lens, wherein the additional material generally matches low dispersion properties of the relatively low dispersion glass;
    still further constructing at least one further lens from a further material different from the relatively low dispersion glass and the additional material; and
    positioning a first plurality of lenses comprising a positive lens on one side of a gap and a second plurality of lenses comprising a negative lens on another side of the gap, wherein the first plurality of lenses inserts a significant amount of color, and the gap and second plurality of lenses substantially cancel the significant amount of color;
    wherein dimensions of the first plurality of lenses, gap, and second plurality of lenses are selected to reduce lateral color and decrease centroid shifting due to different colors encountered during inspection.

2. The method of claim 1, wherein the further material provides a relatively small amount of lens power and exhibits a significantly different dispersion power from the relatively low dispersion glass and the additional material.

3. The method of claim 1, wherein the relatively low dispersion glass comprises one from a group comprising calcium fluorite, FPL51, and FPL53.

4. The method of claim 3, wherein the additional material comprises silica.

5. The method of claim 4, wherein the further material comprises a highly dispersive high index flint glass.

6. The method of claim 1, wherein the first plurality of lenses is opposite in sign from the second plurality of lenses.

7. A high order color correction specimen inspection apparatus, comprising:
    at least one lens constructed from a relatively low dispersion glass;
    at least one additional lens constructed from an additional material different from the relatively low dispersion glass of the at least one lens, wherein the additional material generally matches low dispersion properties of the relatively low dispersion glass of the at least one lens; and
    at least one further lens constructed from a further material different from the relatively low dispersion glass and the additional material;
    wherein a first plurality of lenses comprises a positive lens and is positioned on one side of a gap and a second plurality of lenses comprises a negative lens and is positioned on another side of the gap, and further wherein the first plurality of lenses causes an introduction of a significant amount of color, and the gap and second plurality of lenses substantially cancel the significant amount of color and dimensions of the first plurality of lenses, gap, and second plurality of lenses are selected to reduce lateral color and decrease centroid shifting due to different colors encountered during inspection.

8. The apparatus of claim 7, wherein the further material provides a relatively small amount of lens power and exhibits a significantly different dispersion power from the relatively low dispersion glass and the additional material.

9. The apparatus of claim 7, wherein the relatively low dispersion glass comprises one from a group comprising calcium fluorite, FPL51, and FPL53.

10. The apparatus of claim 9, wherein the additional material comprises silica.

11. The apparatus of claim 10, wherein the further material comprises a highly dispersive high index flint glass.

12. The apparatus of claim 7, wherein the first plurality of lenses is opposite in sign from the second plurality of lenses.

13. An objective, comprising:
    a plurality of lenses constructed from at least one predetermined lens material; and
    wherein a first plurality of lenses comprising at least one positive lens is positioned on one side of a gap and a second plurality of lenses comprising at least one negative lens positioned on another side of the gap, and further wherein the first plurality of lenses causes an introduction of a significant amount of color into the objective, and the gap and second plurality of lenses substantially cancel the significant amount of color, and dimensions of the first plurality of lenses, gap, and second plurality of lenses are selected to reduce lateral color and decrease centroid shifting due to different colors encountered by the objective.

14. The objective of claim 13, wherein the plurality of lenses comprises at least one lens constructed from a relatively low dispersion glass.

15. The objective of claim 14, wherein the plurality of lenses further comprises at least one additional lens constructed from an additional material matched with and different from the relatively low dispersion glass.

16. The objective of claim 15, wherein the plurality of lenses further comprises at least one further lens constructed from a further material different from the relatively low dispersion glass and the additional material.

17. The objective of claim 16, wherein the further material provides a relatively small amount of lens power and exhibits a significantly different dispersion power from the relatively low dispersion glass and the additional material.

18. The apparatus of claim 14, wherein the relatively low dispersion glass comprises one from a group comprising calcium fluorite, FPL51, and FPL53.

19. The apparatus of claim 15, wherein the additional material comprises silica.

20. The apparatus of claim 16, wherein the further material comprises a highly dispersive high index flint glass.

21. The objective of claim 13, wherein the first plurality of lenses is opposite in sign from the second plurality of lenses.

* * * * *